United States Patent [19]
Tomii et al.

[11] Patent Number: 5,940,173
[45] Date of Patent: *Aug. 17, 1999

[54] METHOD AND APPARATUS FOR INSPECTING THE QUALITY OF TRANSPARENT PROTECTIVE OVERLAYS

[75] Inventors: Syuzo Tomii; Kunio Omura; Michio Shinozaki; Nabuaki Honma; Ken-Ichi Yokoyama, all of Tokyo, Japan

[73] Assignee: Toppan Printing Company Limited, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/934,089

[22] Filed: Sep. 19, 1997

[30] Foreign Application Priority Data

Sep. 19, 1996 [JP] Japan .................................. 8-271871

[51] Int. Cl.$^6$ .................................................. G01N 21/00
[52] U.S. Cl. .......................... 356/237; 356/382; 356/372; 356/445
[58] Field of Search ................................. 356/237, 345, 356/399, 401, 382, 372, 445

[56] References Cited

U.S. PATENT DOCUMENTS

| | | |
|---|---|---|
| 4,522,881 | 6/1985 | Kobayashi et al. . |
| 4,780,348 | 10/1988 | Yamamoto et al. . |
| 4,977,136 | 12/1990 | Fujiwara et al. . |
| 5,217,773 | 6/1993 | Yoshida . |
| 5,326,179 | 7/1994 | Fukai et al. . |
| 5,427,997 | 6/1995 | Oshima et al. . |
| 5,527,759 | 6/1996 | Oshima et al. . |
| 5,646,089 | 7/1997 | Oshima et al. . |
| 5,646,388 | 7/1997 | D'Entremont et al. . |
| 5,675,415 | 10/1997 | Akatsu et al. ................. 356/345 X |
| 5,706,091 | 1/1998 | Shiraishi ............................ 356/399 |
| 5,771,095 | 1/1998 | Prikryl et al. ..................... 356/345 |

FOREIGN PATENT DOCUMENTS

| | | |
|---|---|---|
| 2-144448 | 7/1990 | Japan . |
| 4294195 | 10/1992 | Japan . |

*Primary Examiner*—Robert H. Kim
*Assistant Examiner*—Reginald Ratiff
*Attorney, Agent, or Firm*—Graham & James LLP

[57] ABSTRACT

A method and apparatus for inspecting the quality of transparent protective overlays. The inspection method and apparatus enables accurate inspection of formed transparent protective overlays and enables implementation of more quantitative control of transparent protective overlay quality. Such method and apparatus automatically and accurately inspects the quality of transparent protective overlays placed on substrate surfaces to determine whether the transparent protective overlay formed to protect information such as images, text, or symbols recorded on the surface of a card-type or other easily portable information-recorded medium is of acceptable quality.

21 Claims, 7 Drawing Sheets

[Key]

1 Intensity of reflect light

2 Defective area in transparent protective overlay

METHOD AND APPARATUS FOR INSPECTING THE QUALITY OF TRANSPARENT PROTECTIVE OVERLAYS

TECHNICAL FIELD OF THE APPLICATION

This invention concerns an inspection method suited to automatically and accurately inspect the quality of transparent protective overlays placed on substrate surfaces and an inspection apparatus for that purpose, specifically, a method and apparatus for inspecting whether the transparent protective overlay formed is of good quality when a transparent protective overlay to protect information such as images, text, or symbols recorded on the surface of a card-type or other easily portable information-recording medium, where information such as images, text, or symbols is recorded on the surface, such as company, student, or organization ID cards, driver's licenses, automated teller machine cards, credit cards, bank cards, or the like.

BACKGROUND OF THE INVENTION

There are many devices in use in easily portable card form, such as company, student, or organization ID cards and licenses that bear personal information including images such as portraits of the bearer and text and symbols such as the name and affiliation of the bearer. There are also many cards such as automated teller machine cards, credit cards, and other bank cards with these same characteristics for which security is an important concern and which bear images such as portraits of the bearer and personal information in text and symbols. Most of these cards are covered with a transparent protective overlay.

This applies to cards, but also to many other products. To meet demands on the part of users (who want to be able to get good quality products quickly) and suppliers (who want to be able to produce these cards most profitably), it is extremely important to supply products at low cost and in short periods of time by achieving high productivity by producing mass quantities of product faster and with a higher rate of good products.

For image information or information composed of text and symbols recorded on a card surface, various well known methods have already been proposed for techniques to inspect the recording quality (print quality) and techniques to inspect whether the contents that are recorded on the card match the images, text, or symbols that were supposed to be printed on the card surface. Such well known methods do not inspect transparent protective overlays. Two such examples are Utility Model Announcement H02 (1990)-144448 (Omura, et al., "Card Text and Image Printing Device," Japan, Utility Model Registration Application) and U.S. Pat. No. 5,646,388 (D'Entremont, et al., "Systems and Method for Recording Data," USA, Patent Application, patent families WO 9610798 and AU 9538267). Both of these methods send a card recorded with the images, text, or symbols on the card surface whose card surface images, text, or symbols are to be inspected to an inspection stage by means of a card conveyor mechanism. An inspection light is then shone on the area to be inspected on the card, the reflected light thus obtained is picked up by a means of inspection such as a CCD, and data from the reflected light received is data processed to determine whether the card, not including the transparent protective layer, is good.

Ideal quality for a transparent protective overlay is generally determined by several factors: is it of uniform thickness, is it formed only where intended, and are outlines sharp in the viewed area. In practice, however, they may not be ideally formed. Some of the possible causes include the obvious, such as the method of forming the transparent protective overlay or the conditions, as well as possibilities such as the layer structure of the transparent protective overlay (material and structure), the material of the object the layer is formed on, and problems of physical compatibility caused by the relationship between the states of the surfaces involved. Some examples of poor quality include transparent protective overlays that are formed unevenly, areas where transparent protective overlay should be formed but isn't, transparent protective overlay that is formed in areas where it is not necessary (flash and misalignment of transfers), damage to the transparent protective overlay formed, and air bubbles formed between the object surface and its transparent protective overlay. These problems may be fewer or greater, but statistically speaking, they always appear to some degree.

For cards on which recorded images, text, and symbols are protected by a transparent protective overlay, it is very important that quality control of the transparent protective overlay be performed highly efficiently if demands for supplying large quantities at low cost in short periods, as described previously, are to be met.

As things stand now, conventional inspections determine if transparent protective overlays placed on cards to protect images, text, or symbols recorded by printing or the like under the systems currently in widespread use meet quality standards relies solely on a visual inspection of the transparent protective overlay by a trained inspector. Under current practice, the inspection is dependent on this person.

This conventional system has problems of nonuniform application of inspection standards, since inspectors will vary in terms of skill, their physical or mental condition may vary on any given day, and the transparency of the film makes inspection difficult. There is also an upper limit to how many units can be inspected in a given period of time so that further improvements are unattainable.

SUMMARY OF THE INVENTION

It is difficult to establish a stable level of quality control for transparent protective overlays because the conventional inspection means for transparent protective overlays depend on the techniques previously described and the quality of the transparent protective overlay being controlled is heavily influenced by the experience and training of the inspectors. To mass-produce products that have transparent protective overlays (such as cards) thus requires considerable personnel expenses for the inspectors needed for quality control since the number of good inspectors has to be increased alongside the increased production. This creates a multiplier effect that makes it difficult to have low cost of transparent protective overlays alongside highly efficient quality control. This becomes a major factor in declining productivity.

The purpose of this invention is to provide an inspection method and apparatus that will enable accurate inspection of formed transparent protective overlays at a stable level. This will, for example, stabilize quality control of transparent protective overlays, reduce expenses for transparent protective overlay inspection and quality control, increase productivity in mass-production of products in which transparent protective overlays are formed by increasing the efficiency of related tasks, and enable implementation of more quantitative control of transparent protective overlays quality.

Cards, documents, and other types of easily portable information storage media on which information such as images, text, or symbols are recorded and covered with a transparent protective overlay to protect the image, text and symbol information are good examples of products on which transparent protective overlays are formed. Some such cards might be used to attest that the holder is the rightful owner of the card or attest to the owner's identity. In such cases, information such as the owner's face and name is printed on the card. Since most of such cards are carried at all times and used indoors and outdoors in daily life, the card surface is regularly subjected to both the elements and wear. If the image is printed through sublimation transfer, the image is thus subjected to ultraviolet radiation and naturally tends to fade readily so that it becomes steadily more difficult to discern the information recorded on the card, such as the face or name. This can also make it easier to unlawfully alter the information recorded on the card. For these reasons, cards that are imprinted with a portrait of the holder or other information about the holder are covered with a transparent protective overlay formed in the printed surface to inhibit the aforementioned wear and fading, to prevent unlawful alteration, and to make the recorded images, text, or symbols easily readable.

A multi-layer structure of transparent protective overlay of layers composed of suitable material is often used to increase the effectiveness of protection of the aforementioned images, text, or symbols, to provide durability against environmental factors such as wear, chemicals, and light, or to increase such durability. When the recorded images, text, or symbols are recorded by sublimation transfer using sublimation dyes, a layer containing agents that absorb ultraviolet radiation is often included in parts of the transparent protective overlay to effectively prevent the loss of color through fading of the recorded images, text, or symbols. For example, ultraviolet light falling onto the card may be absorbed before reaching the image in order to protect the image from ultraviolet radiation. To prevent counterfeiting or alterations of cards, a layer that is especially difficult to counterfeit or alter is often included in part of the transparent protective overlay. For example, a decorative layer with a diffraction grating or hologram is quite often placed in the transparent protective overlay.

FIG. 6 shows an example in which a transparent protective overlay is placed on a card as described above. Card 1 is constructed of a card substrate 101, which is a material such as polyvinyl chloride (PVC), onto the surface of which information such as images, text, or symbols is recorded by some means of printing (usually, sublimation transfer, thermal fusion transfer, injection, electrophotography, transfer foil, or the like). Transparent adhesive layer 1a and protective layer 1b are then formed on that surface in that order. Transparent adhesive layer 1a and protective layer 1b together form the transparent protective overlay, through which the aforementioned information recorded on the surface of card substrate 101 can be seen.

FIG. 7 shows an example with a transparent protective overlay with a somewhat different layer structure from FIG. 6. As in FIG. 6, information composed of images, text, and symbols is recorded on the surface of card substrate 101. On top of that surface are formed, in order, transparent adhesive layer 1a, ultraviolet radiation absorbing layer 1e in which an ultraviolet absorbing agent is diffused, intermediate layer 1d, and separative/protective layer 1c. In this example, the layer structure of the transparent protective overlay is composed of adhesive layer 1a, ultraviolet radiation absorbing layer 1e, intermediate layer 1d, and separative/protective layer 1c. Intermediate layer 1d may be placed between ultraviolet radiation absorbing layer 1e and separative/protective layer 1c to reinforce their adhesive strength through its anchoring effect, to prevent re-diffusion of the coloring agent, or for a variety of other reasons. The material is selected according to its intended effect. The aforementioned separative/protective layer 1c is a layer whose separation characteristics are exploited during transfer in the many cases in which overlays are applied through transfer when forming a transparent protective overlay on a card or the like. It also has the function of protecting the images, text, or the like when placed on the outermost surface.

In the examples of FIGS. 6 and 7, the example has stated that information such as images, text, or symbols are recorded on the surface of card substrate 101, but this is not the only possibility. It is sometimes more appropriate to record information such as images, text, or symbols by printing it on adhesive layer 1a, in which case adhesive layer 1a functions as both adhesive layer and image bearing layer and the image is recorded by printing this layer. The location where the information is recorded (the location where the ink, dyes or pigment is located) may be either the top, bottom, or middle of adhesive layer 1a, as shown in the figure. To print in such cases, the surface of adhesive layer 1a of the transparent protective overlay is printed before attachment of the transparent protective overlay to the surface of card substrate 101, then the surface of adhesive layer 1a is aligned with the surface of card substrate 101 and attached or transferred to create the transparent protective overlay that protects the images. When sublimation transfer is used as the printing method, the formation of the images, text, or symbols recorded by incorporation of sublimation dyes into the image-receiving layer is the same when the image-receiving layer is card substrate 101 or a layer placed on card substrate 101 or when adhesive layer 1a doubles as the image-receiving layer. When adhesive layer 1a doubles as the image-receiving layer and the image is recorded on the top surface as shown in the figure, a variety of methods can be employed, such as printing onto the top surface of adhesive layer 1a after it is placed on card substrate 101 and then applying another layer to create the transparent protective overlay, placing the other layer used to form the transparent protective overlay on top of adhesive layer 1a after it has been printed and then attaching them both to card substrate 101, or by attaching the unprinted side of adhesive layer 1a after it has been printed to card substrate 101 and then attaching the other layer that will complete the transparent protective overlay onto it.

As a supplementary note, when sublimation transfer recording is used, either card substrate 101 can be a material that is receptive to the sublimation dyes (which may include but is not limited to such well known receptive materials as PVC and polyester resins) or a layer that is receptive to sublimation dyes can be placed on the surface of the card substrate and used as the receptive layer. This allows images, text, or symbols to be formed using sublimation dyes on card substrate 101 itself or on the layer placed atop the surface of the card substrate, the layer in question being used as the receptive layer to which images, text, or the like is formed by sublimation transfer recording directly to the layer.

Currently known adhesive materials may be used for adhesion. For example, both materials that exhibit adhesiveness when heated, pressurized, or pressurized under heat, and materials that exhibit adhesiveness when simply painted on and then dried under pressure can be used. Protective layer 1b in FIG. 6 and ultraviolet radiation absorbing layer 1e, intermediate layer 1d, and separative/protective layer 1c in FIG. 7 have eave-like protruding cross-sections in the figures, but do not have to have this structure in practice. The characteristics of the materials used and the transparent protective overlay structure may permit a transparent protective overlay that is cut smoothly from the top edge to the bottom edge, with no eave-like protrusions.

This invention proposes the following technology to achieve the aforementioned goals.

First, the method of inspecting the transparent protective overlay is characterized by irradiating a substrate surface onto which a transparent protective overlay that possesses characteristics of responding to a specific wavelength band with a light that has a peak at the aforementioned specific wavelength band, detecting the intensity distribution of the light on the aforementioned substrate surface which varies according to whether the aforementioned transparent protective overlay is good or defective because of the aforementioned characteristics of the aforementioned irradiated light and the aforementioned transparent protective overlay, and inspecting the quality of the transparent protective overlay formed on the aforementioned substrate surface based on the aforementioned detected distribution of light intensity.

The transparent protective overlay that possesses characteristics of responding to the specific wavelength band may have properties of absorbing light, reflecting light, or emitting a different wavelength of light (which may, in addition to visible light, be ultraviolet, infrared, or electromagnetic radiation) when the material used for any part of it is irradiated with light of the specific wavelength band (which may, in addition to visible light, be ultraviolet, infrared, or electromagnetic radiation). These characteristics of responding to a specific wavelength band may be imparted to the transparent protective overlay by 1 diffusing in any of the layers a material with appropriate absorbency if the specific wavelength band is to be absorbed, or 2 diffusing in any of the layers a material with appropriate reflectivity if the specific wavelength band is to be reflected, or 3 diffusing in any of the layers a material that has the property of emitting a different wavelength band of light if the specific wavelength band is to cause a different wavelength to be emitted. Other methods are also possible, such as creating an optically multi-layered film in part of or throughout the transparent protective overlay that reflects or absorbs an incoming specific wavelength band of light.

This invention is also characterized by a transparent protective overlay as described above that contains an absorbent material for absorbing a specific wavelength band of light. For example, this may be achieved by diffusing at an appropriate ratio an absorbent material that absorbs a specific wavelength band of light in some or all of the layers that comprise the transparent protective overlay.

Some examples of materials that possess the property of absorbing ultraviolet radiation are Ciba-Geigy's Tinuvin 326, Tinuvin 327, and Tinuvin 328. All of these materials absorb in the wavelength band of approximately 300–400 μm.

Some example of materials that have the property of absorbing infrared radiation are inorganic materials elements such as vitreous powders that contain one or both of bivalent iron ions ($Fe^{2+}$) and bivalent copper elements ($Cu^{2+}$). These vitreous powders are formed primarily of diphosphorus pentoxide ($P_2O_5$) that contain at least 1.0% by weight of one or both of iron oxides and copper oxides; even better is 35.0–80.0% diphosphorus pentoxide by weight and 0.3% or less by weight each of iron oxides and copper oxides.

Examples that absorb less visible light than the vitreous powders described above and has excellent infrared absorption are white crystalline materials such as phosphate type white crystalline powders and sulfate type white powders that have diphosphorus pentoxide ($P_2O_5$) as their main ingredient and 20% by weight or more of one or both of bivalent iron ions ($Fe^{2+}$) and bivalent copper elements ($Cu^{2+}$); even better is to have a diphosphorus pentoxide ($P_2O_5$) content of 40–70% by weight and 30–70% by weight [sic] one or both of bivalent iron ions ($Fe^{2+}$) and bivalent copper elements ($Cu^{2+}$).

The aforementioned vitreous powders and phosphate type white crystalline powders may also contain any of the following elements if necessary.

$Al_2O_3$ 2.0 to 10.0% by weight
$B_2O_3$ 1.0 to 30.0% by weight
MgO 3.0 to 10.0% by weight
ZnO 0 to 3.0% by weight
$K_2O$ 0 to 15.0% by weight
BaO 0 to 10.0% by weight
SrO 0 to 10.0% by weight
Ni, Co or Se Trace amounts Dyes are also available as infrared absorbing materials. For example, a white reaction product that contains either or both of tungsten hexachloride and phosphate ester/phosphorous acid can be used.

Among organic materials, some infrared-absorbing materials are the polymethine pigments (including cyanine pigments), of which the pyryliums and thiopyryliums are ideal. Other possibilities include phthalocyanines, dithiol metallic salts, naphthaquinone, anthraquinones, triphenylmethanes (and similar), aminiums and di-inmoniumums.

All of these exhibit good absorbency of light in infrared wavelengths.

Recording by sublimation transfer is know for the ease with which it can produce beautifully photographic color images with rich half-tones. With cards like the aforementioned, the unique data such as the face and name of the owner to be recorded on the card normally varies from card to card, so printing by sublimation transfer, which allows recording in which it is easy to change unique data such as beautiful color images from card to card, is one typical method of printing that is used on cards. Since images and the like recorded by sublimation transfer use sublimation dyes for the coloring material, normally an ultraviolet light absorbing material is diffused in at least one of the layers of the transparent protective overlay to prevent ultraviolet radiation image fading by absorbing ultraviolet radiation so that it does not shine onto the sublimation dye image. Inspection of the transparent protective overlay of cards with images recorded through sublimation transfer exploits the fact that there will be a layer diffused with an ultraviolet absorbing material in at least part of the transparent protective overlay to get intensity distribution data for reflection of the ultraviolet radiation irradiated onto the transparent protective overlay to be inspected. This data is then analyzed to enable a suitable inspection.

This invention is also characterized by including in the aforementioned transparent protective overlay a marker material that emits light in response to light of a specific wavelength and thereby obtaining the aforementioned light intensity distribution from the light emitted by the marker. The marker material that emits light in response to light of a specific wavelength may, for example, be a fluorescent material that has the property of emitting fluorescent light when it receives light of a specific wavelength band.

Infrared fluorescent material that emits fluorescent light upon receiving infrared light and ultraviolet fluorescent material that emits fluorescent light upon receiving ultraviolet light are typical examples of such marker materials.

Infrared fluorescent materials also include infrared-visible converting fluorescent materials, which emit visible light when excited by infrared radiation and those which emit longer wavelengths (980 to 1020 nm) when excited by infrared radiation (wavelengths of about 800 nm).

The former (infrared-visible converting fluorescent materials) are fluorescent materials that have very special excitation mechanisms that excite the emission of visible light by using multiple photons of low-energy infrared radiation. There are two types of mechanisms. The first enables a high excitation through another stage of excitation in the activator ion; the second enables a high excitation by multiple resonant energy transfers from the sensitizing agent. The first type is observed in the many host crystals when $Er^{3+}$ or $Ho^{3+}$ is the activator; in the second type, the sensitizing agent $Yb^{3+}$ absorbs infrared and excites $Er^{3+}$, $Tm^{3+}$, $Ho^{3+}$, or the like at the center of light emission to a high level by another stage of energy transfer. For example, $YF_3$:Yb+Er, $YF_3$:Yb+Tm, or BaFCl:Yb+Er can be used. Here, the fluorescent agent is usually indicated by its composition and is notated by separating the host crystal that is the main ingredient with a colon (:) from the activator or light emission center that is diffused within it. For example, ZnS:Mn indicates that the host crystal is ZnS and the activator is Mn.

The latter (which emits light in longer wavelengths (980–1020 nm) upon excitation by infrared (800 nm)) has many possible compositions that may be used:

$LiNd_{0.9}Yb_{0.1}P_4O_{12}$ $LiBi_{0.2}Nd_{0.7}Yb_{0.1}P_4O_{12}$ $Nd_{0.9}Yb_{0.1}Nd_5(MoO_4)_4$ $NaNd_{0.9}Yb_{0.1}P_4O_{12}$ $Nd_{0.8}Yb_{0.2}Na_5(WO_4)_4$ $Nd_{0.8}Yb_{0.2}Na_5(Mo_{0.5}W_{0.5O4})_4$ $Ce_{0.05}Gd_{0.05}Nd_{0.75}Yb_{0.15}Na_{0.7}(W_{0.7}Mo_{0.3}O_4)_4$ $Nd_{0.9}Yb_{0.1}Al_3(BO_3)_4$ $Nd_{0.9}Yb_{0.1}Al_{2.7}Cr_{0.3}(BO_3)_4$ $Nd_{0.6}Yb_{0.4}P_5O_{14}$ $Nd_{0.8}Yb_{0.2}K_3(PO_3)_2$

Next, the aforementioned ultraviolet fluorescent light-emitting material will be described. Ultraviolet fluorescent light-emitting material is excited by ultraviolet radiation; the peaks in the spectrum emitted when it returns to its lower energy potential can be in the blue, green, red or other wavelength bands. It is formed by high temperature sintering after activators such as trace amounts of metals (copper, silver, manganese, bismuth, lead, etc.) for increasing the strength of the emitted light are added to a highly pure fluorescent substance of zinc sulfide and sulfides of alkaline earth metals. Combination of host crystals and activators can be used to adjust the hue, brightness, and color attenuation. Some possible ultraviolet radiation fluorescent agents are:

$Ca_2B_5O_9Cl$: $Eu^{2+}$ $CaWO_4$

ZnO:Zn $Zn_2SiO_4$:Mn $Y_2S$: Eu

ZnS:Ag $YVO_4$:Eu $Y_2O_3$:Eu $Gd_2O_2S$:Tb $La_2O_2S$:Tb $Y_3Al_5O_{12}$:Ce

They can be used individually or mixed as appropriate. The peak of their fluorescent spectra are in wavelength bands other than blue, green, and red.

The intensity distribution of the reflected light when a transparent protective overlay with the characteristics of responding to a specific wavelength band is irradiated with the aforementioned specific wavelength band can be used to perform a more accurate inspection by the following method, even when there are effects from the images, text, and symbols protected by the transparent protective overlay. In other words, an accurate inspection can be performed by obtaining the intensity distribution of the reflected light of the images, text, and symbols protected by the transparent protective overlay (background data) or similar data separately from the intensity distribution of the reflected light obtained when a transparent protective overlay with the characteristics of responding to a specific wavelength band is irradiated with the aforementioned specific wavelength band that is affected by the protected images, text, and symbols and then correcting the latter data based on the former.

For example, reflected light distribution data from images, text, and symbols formed on the card substrate can be obtained before placing the transparent protective overlay on the product (for example, a card substrate). It is useful to use experiments, simulations, or the like to quantitatively confirm in advance the degree of difference in the intensity distribution data for reflected light obtained with and without the transparent protective overlay and what the relationship is between them. The best irradiation light for obtaining background data is light that is in the wavelength band to which the transparent protective overlay responds as its specific wavelength band, but other wavelength bands also work.

A more accurate inspection can still be performed even after the transparent protective overlay is placed on the product (for example, on the card substrate) by correcting data with the reflected light intensity distribution obtained by irradiating with light of a different wavelength (for example, visible light in an appropriate wavelength band, infrared light, or the like) from the light in the specific wavelength band that the transparent protective overlay responds to that is used for getting the background data for the inspection of the transparent protective overlay.

The transparent protective overlay inspection apparatus of this invention is characterized by having a means of irradiation that irradiates a light that peaks in a specific wavelength band on a substrate surface onto which is formed a transparent protective overlay having the characteristic of responding to the aforementioned specific wavelength band, a means of receiving light that detects the intensity distribution of light in the aforementioned transparent protective overlay create by the variation in good and defective areas of the aforementioned transparent protective overlay from the light irradiated from the aforementioned means of irradiation and the aforementioned characteristics of the aforementioned transparent protective overlay, and a means of determining whether the quality of the transparent protective overlay formed on the aforementioned substrate surface is good or defective based on the light intensity distribution detected by the aforementioned light-receiving means.

This invention is also characterized by the aforementioned transparent protective overlay including an absorbing material that absorbs light in a specific wavelength band, the aforementioned light-receiving means receiving the reflection from the surface of the aforementioned substrate of the light irradiated by the means of irradiation, and the determination of whether the quality of the transparent protective overlay is good or defective using the aforementioned means of determination being made by converting the intensity of the reflected light received by the aforementioned means of receiving light to electrical signals and comparing those signals to reference signals.

This invention is also characterized by the aforementioned transparent protective overlay including a marker material that emit lights in response to light in a specific wavelength band, the aforementioned light-receiving means receiving light emitted from the aforementioned marker material in response to light shone onto it by the aforementioned means of irradiation, and the determination of whether the quality of the transparent protective overlay is good or defective using the aforementioned means of determination being made by converting the intensity of the light received by the aforementioned means of receiving light to electrical signals and comparing those signals to reference signals.

This invention is also characterized by the light having its peak in the aforementioned specific wavelength band being ultraviolet light.

The transparent protective overlay that has the characteristic of responding to a specific wavelength band is as has been previously described.

This invention is also characterized by the aforementioned means of irradiation having a light source that has a peak in a wavelength band different from the aforementioned specific wavelength band, the aforementioned light-receiving means having an optical system and image pick-up element for light in the aforementioned wavelength band and a filter that passes light in the aforementioned wavelength band, and by having a means of detecting images on the substrate that can distinguish images in the aforementioned specific wavelength band from images such as text and images printed on the aforementioned substrate surface using the aforementioned filter and detect the aforementioned printed text and images.

This enables inspection not just of the transparent protective overlay but of the printed text, images, and the like existing under the transparent protective overlay.

Also, as previously described, the reflected light intensity distribution obtained by shining the specific wavelength band light to which the transparent protective overlay responds can be used to perform a more accurate and efficient inspection of the transparent protective overlay even when there are effects from the aforementioned printed text, images, and the like by, for example, obtaining intensity distribution data for reflected light by shining a light in a wavelength band (for example, visible light in an appropriate wavelength band or infrared light) different from the wavelength of the aforementioned light of a specific wavelength band that the transparent protective overlay responds to (background data) and then using this background data to correct the data.

Since variations of good and defective areas in the aforementioned transparent protective overlay produce variations in the intensity distributions of light on the aforementioned substrate surface obtained from irradiated light when a substrate surface on which is formed a transparent protective overlay that responds to a specific wavelength band is irradiated with light that peaks in the aforementioned specific wavelength band under the method of inspecting transparent protective overlay of this invention, the variations in this light intensity distribution can be detected for an efficient and accurate inspection of good and defective transparent protective overlays formed on the aforementioned substrate surface and the results linked to more stable transparent protective overlay quality control and greater efficiency in transparent protective overlay quality control, to greater productivity in the production of products with transparent protective overlays, as well as to implementation of a system that produces and supplies products with transparent protective overlays at lower cost.

Also, because the transparent protective overlay inspection apparatus of this invention enables detection by the light-receiving means of the intensity distribution of light on the aforementioned transparent protective overlay when a substrate on which is formed a transparent protective overlay that responds to a specific wavelength band is irradiated with light that peaks in the aforementioned specific wavelength band by a means of irradiation and enables detection of variation in light intensity distribution caused by variation of good and defective in the aforementioned transparent protective overlay, determination of whether the quality of the transparent protective overlay formed on the aforementioned substrate surface is good or no good can be performed automatically and efficiently based on intensity distribution data of light detected by the aforementioned light-receiving means. It is also possible to determine whether the quality is good or no good quantitatively, so quality control of the aforementioned transparent protective overlays can be automated and accelerated, transparent protective overlay quality control can be stabilized, expenses for transparent protective overlay quality control can be reduced, and transparent protective overlay quality control can be made more efficient.

DETAILED DESCRIPTION OF THE PREFERRED EMBODIMENT

Figure 1:
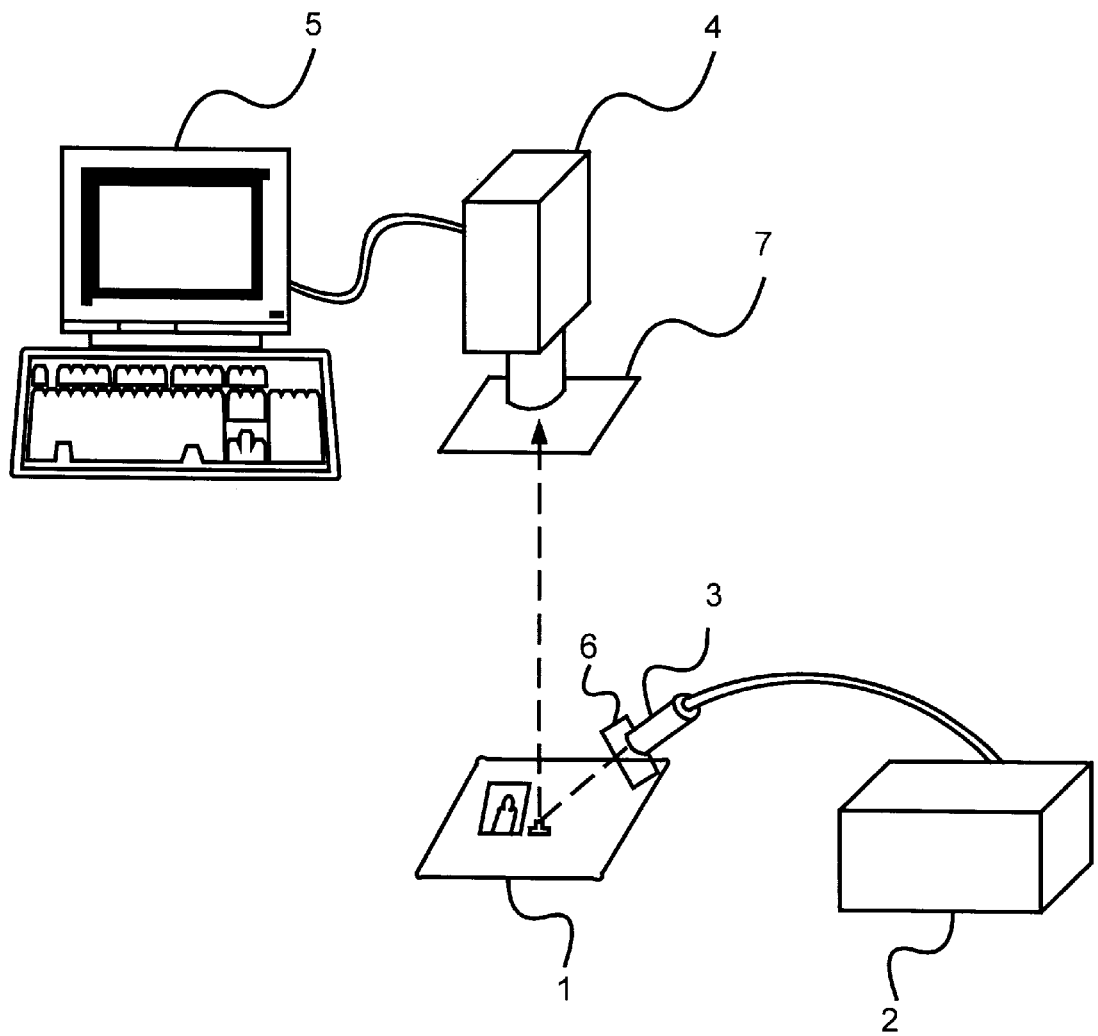
FIG. 1: This figure is a block diagram that shows an example of a trangerent protective overlay inspection apparatus that uses the transparent protective overlay inspection method of this invention.

FIG. 1 is a block diagram that shows an overview of one example of a transparent protective overlay inspection apparatus that uses the transparent protective overlay inspection method of this invention.

This transparent protective overlay inspection apparatus is composed of a light projection unit 3, which irradiates the surface of card 1 on which is formed a transparent protective overlay whose light absorption wavelength area is in the ultraviolet area with ultraviolet light from light source 2, an image pick-up camera 4, which uses a CCD that responds to ultraviolet light to pick up ultraviolet light reflected from card 1, and a data processing device 5, which gets the image data of the card 1 surface picked up with ultraviolet light by image pick-up camera 4 and processes the image.

Projection unit 3 and image pick-up camera 4 can be equipped when necessary with optical filters 6 and 7, which pass the required type of light.

If the transparent protective overlay contains an appropriate amount of ultraviolet absorber mixed by diffusion in at least one of its layers and the resultant absorbing wavelength band is around 350 nm, a light source 2 for about 200 W of ultraviolet radiation would be used. In the diagram, light projection unit 3 and light source 2 are separate units with projection unit 3 linked to light source 2 by light-conducting fiber, but the two can also be constructed as one unit. Either structure may be used, depending on which is more appropriate to the space, parts cost, or performance required by the overall inspection apparatus design.

Figure 6:
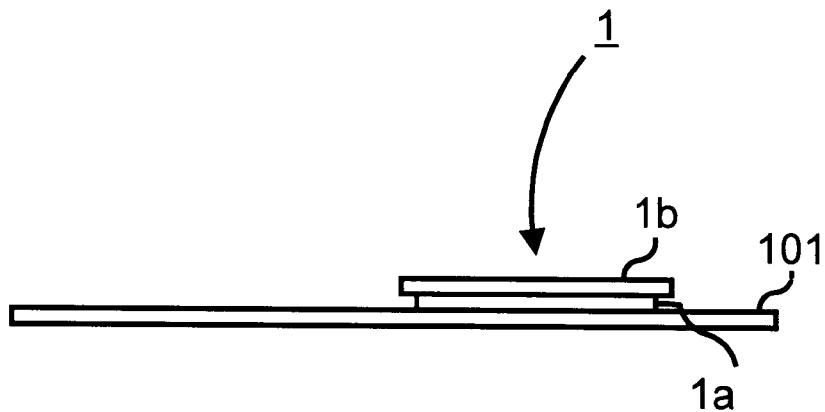
FIG 6: This figure is a structural diagram of a card to be inspected by the transparent protective overlay inspection apparatus in one working embodiment of this invention.
Figure 7:
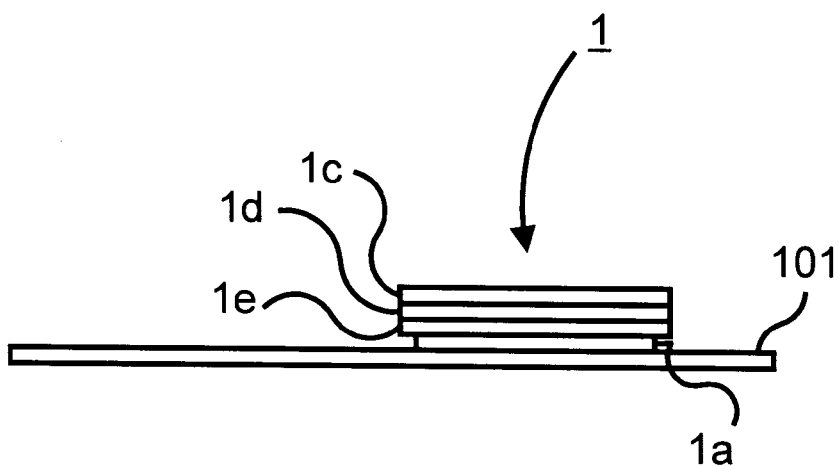
FIG. 7: This figure is a structural diagram of a card to be inspected by the transparent protective overlay inspection apparatus in another working embodiment of this invention.

The structure of card 1 is as shown in FIG. 6. An adhesive layer 1a is attached to the surface of card substrate 101, which is made of a material such as PVC. Transparent protective overlay 1b is formed atop adhesive layer 1a. Alternately, adhesive layer 1a can be formed on the surface of card substrate 101 and an ultraviolet radiation absorbing layer 1e of ultraviolet-absorbing material formed atop layer 1a, an intermediate layer 1d formed atop layer 1e, and a separative/protective layer 1c formed atop layer 1d, as shown in FIG. 7.

Figure 2A:
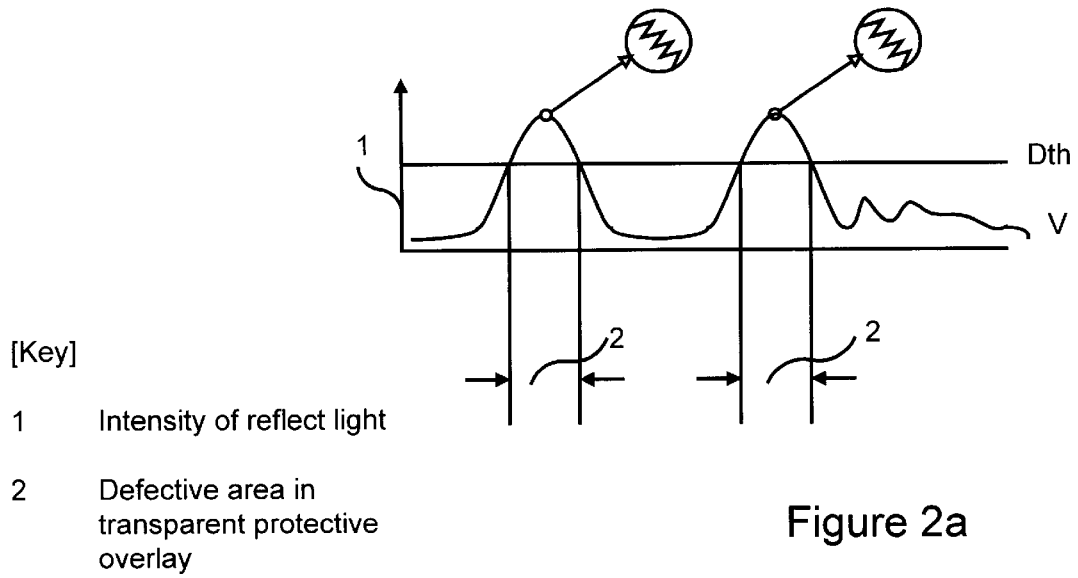
FIG. 2a: This figure is a diagram describing the method of inspecting transparent protective overlays using the transparent protective overlay inspection apparatus to determine if the intensity of light reflected from the transparent protective layer exceeds a maximum Dth level in one working embodiment of this invention.
Figure 2B:
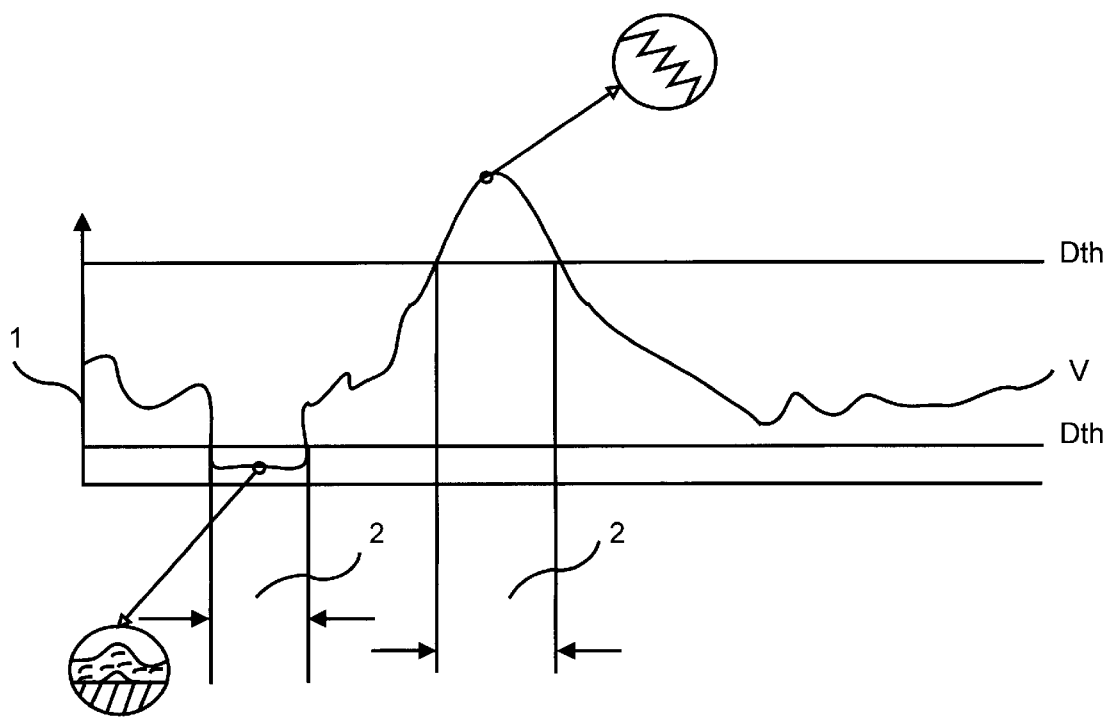
FIG. 2b: This figure is a diagram describing the method of inspecting transparent protective overlays using the transparent protective overlay inspection apparatus to determine if the intensity of light reflected from the transparent protective layer is within a range between a maximum and a minimum Dth level in another working embodiment of this invention.
Figure 3:
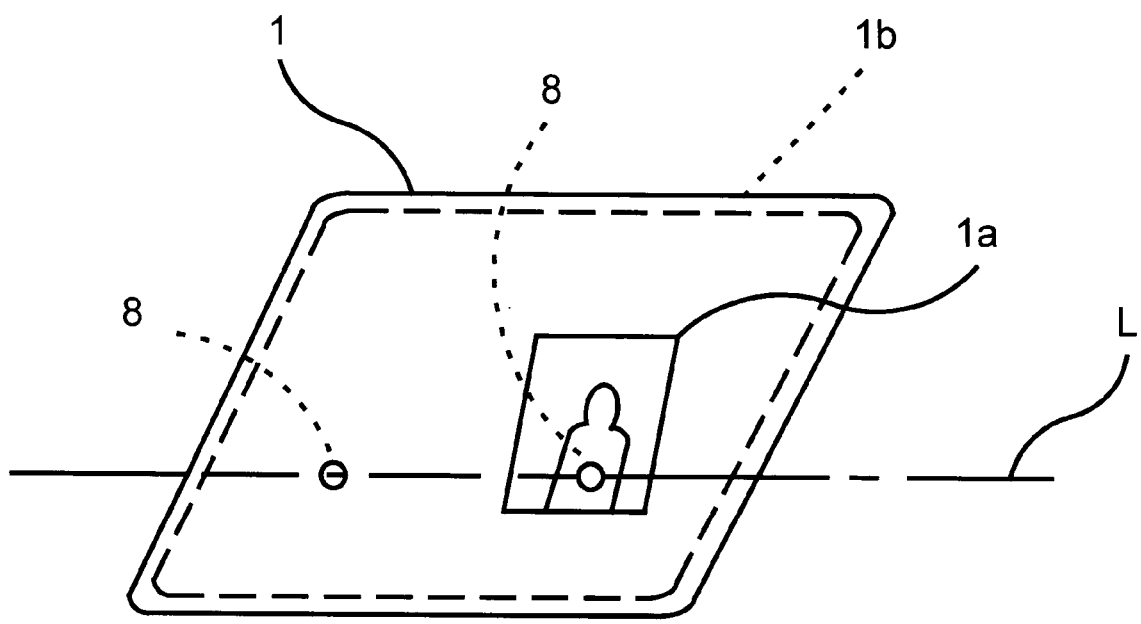
FIG. 3: This figure is a oblique view that shows a card having defective areas in its transparent protective overlay that is to be inspected in the transparent protective overlay inspection apparatus in one working embodiment of this invention.

FIGS. 2a and 2b are diagrams describing the method of inspecting transparent protective overlays using the transparent protective overlay inspection apparatus in two working embodiments of this invention. FIG. 3 is a oblique view that shows a card having defective areas in its transparent protective overlay that is to be inspected in the transparent protective overlay inspection apparatus in one working embodiment of this invention.

Prior to scanning a card to inspect the transparent protective overlay, a decision level (Dth), as shown in FIG. 2a, is determined that identifies the maximum level of light intensity that a card having good and/or acceptable transparent protective overlay reflects when a light is shone on it. Determinative of the light intensity reflected by a card include the materials of the transparent protective overlay, and the type of light used to irradiate the substrate surface of the card.

In another exemplary embodiment, which is not limiting, maximum and minimum decision levels (Dth), as shown in FIG. 2b, are determined that identify the range of light intensity of a card having good and/or acceptable transparent protective overlay reflects when a light is shone on it.

In order to determine or to verify the Dth level or levels as shown in FIGS. 2a and 2b, the inspection apparatus of the present invention is used to test cards known to have transparent protective overlays of good and/or acceptable quality. Hence, the known specifications of the materials of the transparent overlay of a card, the type of irradiated light, and tests performed on cards having good and/or acceptable transparent protective overlays identify the Dth level. Once determined, the data processing device 5 of FIG. 1 uses the Dth level to determine if a transparent protective overlay of a card is defective.

Card 1 is scanned on scan line L as shown in FIG. 3. In this case, the positional relationship of projection unit 3 and image pick-up camera 4 of FIG. 1 to the card surface can be kept constant and card 1 moved two-dimensionally by a card drive mechanism (not shown) to scan transparent protective overlay 1b, or projection unit 3 and image pick-up camera 4 can be moved relative to the card surface to scan transparent protective overlay 1b.

The intensity of reflected ultraviolet light indicated by the image data V output by image pick-up camera 4 when the transparent protective overlay of card 1 is scanned on scan line L shows low values at the locations where the transparent protective overlay is formed properly and thus absorbs ultraviolet light in the transparent protective overlay and high values at the defective areas 8 where the card surface reflects more light, as shown in FIG. 2a.

Data processing unit 5 compares the levels of image data V indicating the intensity of reflected ultraviolet light to the slice level for the good/no good decision Dth; areas of the transparent protective overlay on the card surface beyond the slice level for the good/no good decision Dth are judged defective.

Figure 4:
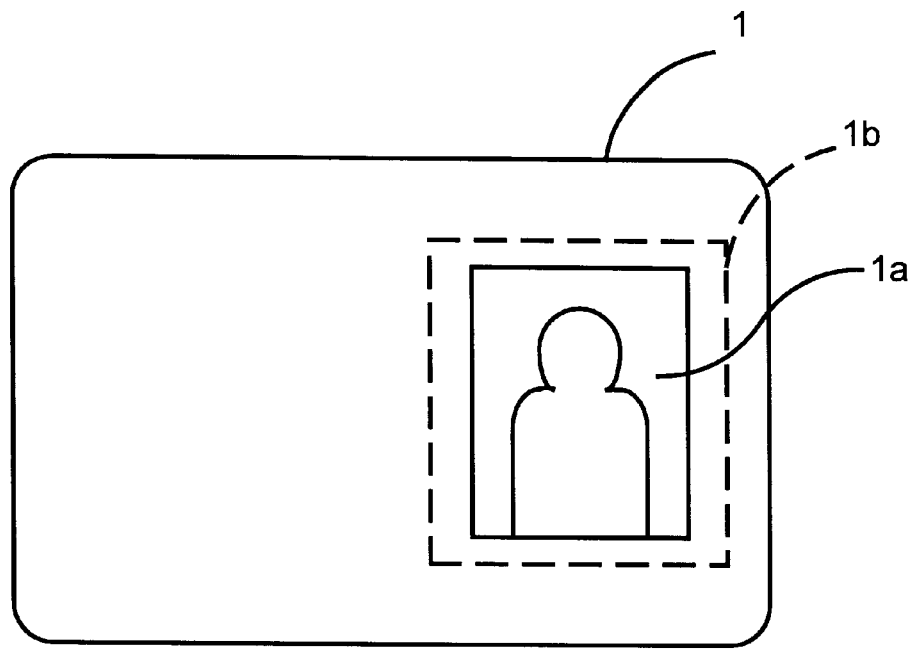
FIG. 4: This figure is a plan view of a card that has a transparent protective overlay formed on part of its surface that is to be inspected in the transparent protective overlay inspection apparatus in one working embodiment of this invention.
Figure 5:
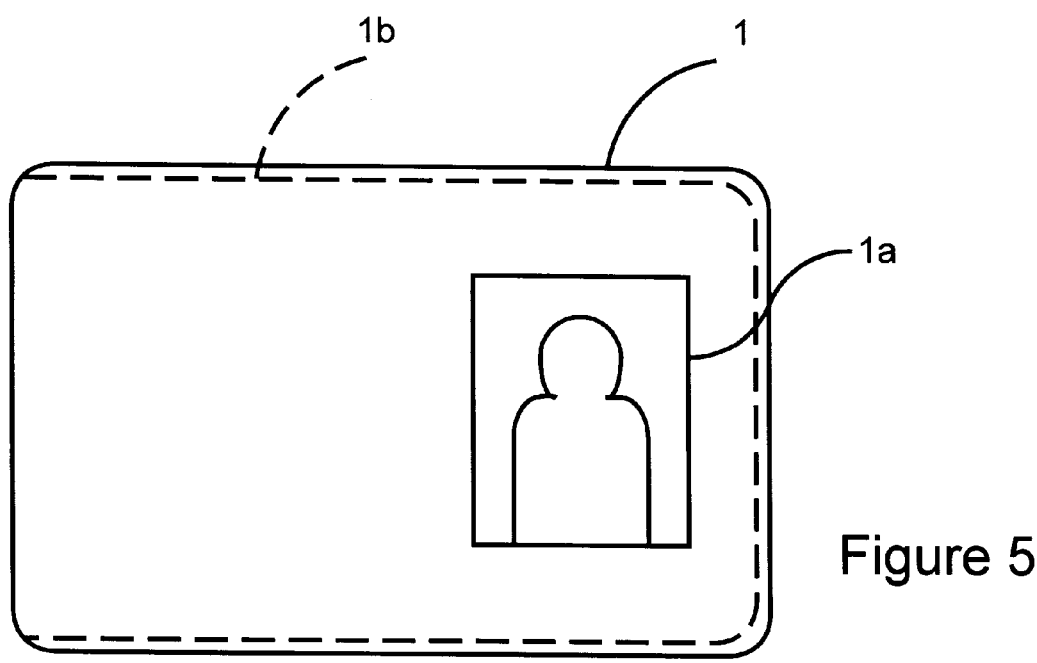
FIG. 5: This figure is a plan view of a card that has a transparent protective overlay formed on all of its surface that is to be inspected in the transparent protective overlay inspection apparatus in one working embodiment of this invention.

In such cases, if the positioning of card 1 within the field of vision of image pick-up camera 4 is accurate, the areas where the transparent protective overlay of the card 1 surface can be scanned, the defective areas of the transparent protective overlay determined, and cards that have defects in the transparent protective overlay identified, regardless of whether the card is formed with partial transparent protective overlays as in FIG. 4 or full transparent protective overlays as in FIG. 5.

In the working embodiments described above, the surface of card 1 on which is formed a transparent protective overlay that has an absorption wavelength area in the ultraviolet wavelengths is irradiated with ultraviolet light and defective transparent protective overlays or defective areas are identified or detected based on the resulting reflected light intensity distribution data. In some cases, however, it may be more appropriate to use infrared instead of ultraviolet. In such cases, the light source 2 should be structured to emit infrared light, the transparent protective overlay should be made to absorb infrared light, and the CCD used in the image pick-up camera should have its sensitivity peak in the infrared wavelength band. The means to give the transparent protective overlay characteristics for absorbing infrared were described earlier; the optimum method may be used. It is easy, for example, to diffuse an appropriate amount of an infrared radiation absorber in one or more of the layers in the transparent protective overlay structure.

In the working embodiments described above, defective areas of the transparent protective overlay were identified based on the intensity of light reflected from a card surface on which a transparent protective overlay was formed, but defective areas of the transparent protective overlay can also be identified by detecting variations in light emitted by the transparent protective overlay if marker materials that react to light rays of specific wavelengths by emitting light of a specific color are mixed into the transparent protective overlay and the transparent protective overlay are then irradiated with light rays of the aforementioned specific wavelength.

Light source 2 can also be constructed so that it has light sources that produce light in the ultraviolet wavelength band and the visible light wavelength band and switch between production of the ultraviolet wavelength band and the visible light wavelength band; in this case, the image pick-up camera 4 should have a first CCD with a sensitivity peak in the ultraviolet wavelength band and a second CCD with a sensitivity peak in the visible light wavelength band with a half mirror to split the light reflected at the card surface to pick up images from the card surface from the split reflected light with the aforementioned first CCD and second CCD.

To pick up the image of the card surface with the first CCD, shine ultraviolet light; to pick up the image of the card surface with the second CCD, shine visible light. Defects of the transparent protective overlay can be detected based on image data obtained from the aforementioned first CCD for transparent protective overlays that absorb light in the ultraviolet wavelength and then text and images printed on the card surface can be detected, identified, and evaluated for defects based on image data obtained from the aforementioned second CCD.

Light source 2 may also be constructed so it produces light from the ultraviolet wavelengths to the visible light wavelengths and image pick-up camera 4 then constructed so that reflected light is split by a half mirror and half passed through a filter that transmits ultraviolet light wavelengths so that it is received by the aforementioned first CCD to get the image of the card surface from reflected ultraviolet light while the second half is passed through a filter that transmits visible light wavelengths to get an image of the card surface at the second CCD from reflected visible light. When the light source 2 produces infrared light wavelengths and visible light wavelengths, the structure of pick-up camera 4 is the same as described above for the aforementioned ultraviolet light but constructed instead for infrared light wavelengths and visible light wavelengths.

In the above examples, line CCDs that match the resolution of the image are used for the CCDs. For example, for 12 dots/mm, a 4X 46 dots/mm is used to prevent moir and fetch an image for card sizes of 5000 pixels or more by scanning according to the resolution. The interface for image pick-up camera 4 and data processing unit 5 fetches image-able data to data processing unit 5 at high speed of 1 line per 1 msec using a fast-processing bus such as a PCI bus.

In working embodiments like those described above, defects of transparent protective overlays formed over the entire printed card surface or a specific part of it can be evaluated for defects based on intensity distributions of light reflected when the card surface is irradiated with ultraviolet or infrared light. By combining it with a card conveyor mechanism, evaluation of transparent protective overlay defects can be automated for greater efficiency.

Defects of transparent protective overlay formed over the entire printed card surface or a specific part of it can also be evaluated for defects based on variations in emitted light by marker materials in the area where the transparent protective overlay is formed and intensity distributions of light emitted by marker materials. By combining it with a card conveyor mechanism, evaluation of transparent protective overlay defects can be automated for greater efficiency.

Text and images printed on the card surface can be detected, identified, and evaluated for defects in parallel to the evaluation of the transparent protective overlay for defects.

Figure 8:
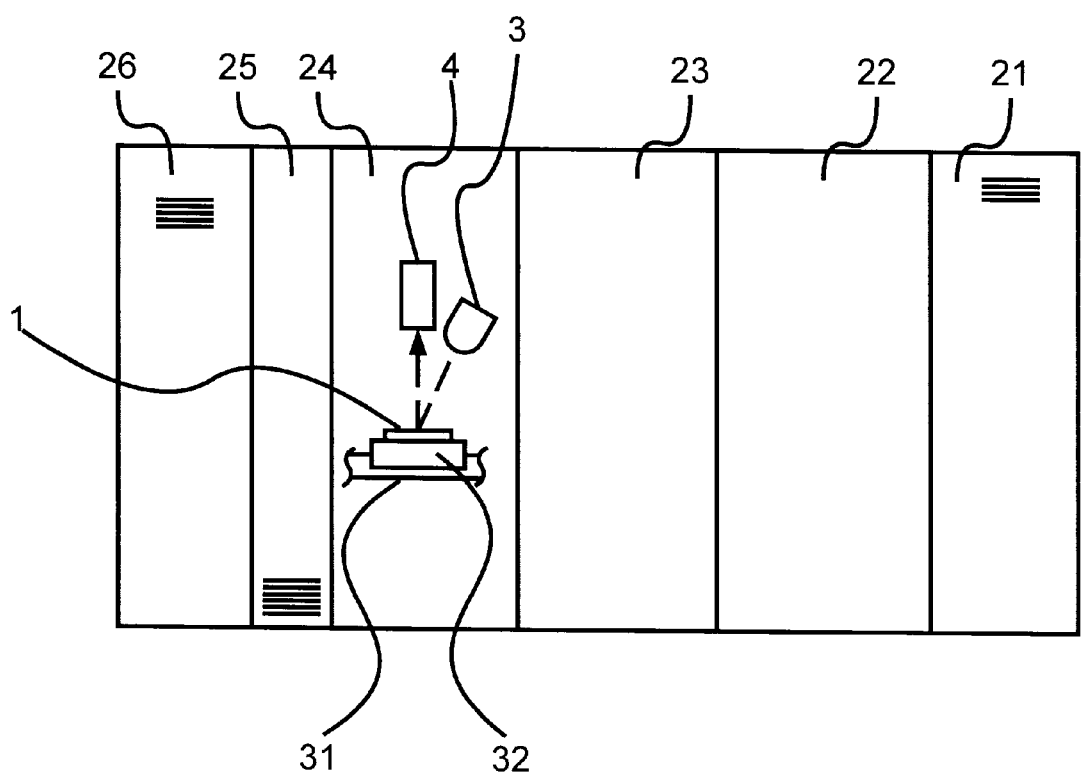
FIG. 8: This figure is a schematic diagram that shows a card manufacturing device that includes the transparent protective overlay inspection apparatus in one working embodiment of this invention in overview.

FIG. 8 is a schematic diagram that shows a card manufacturing device that includes the transparent protective overlay inspection apparatus in one working embodiment of this invention in overview.

This card manufacturing device is composed of a card hopper 21 that feeds cards one at a time, a card print unit 22, a transparent protective overlay former 23 that forms the transparent protective overlay in a specified location on the card surface, a transparent protective overlay scanner 24 that detects defects in the formed transparent protective overlay, a defective card ejector 25 that identifies cards found to have defective transparent protective overlays and ejects them, and a card stacker 26 that holds cards found to have good transparent protective overlays. The transparent protective overlay inspection apparatus is placed in transparent protective overlay scanner 24. The cards may, for example, be fixed in a specified position on stage 32 and brought directly under image pick-up camera 4 by moving stage 32 on conveyor rail 31 where the inspection of the transparent protective overlay formed for defects is performed in an image data processing unit (not shown).

Figure 9:
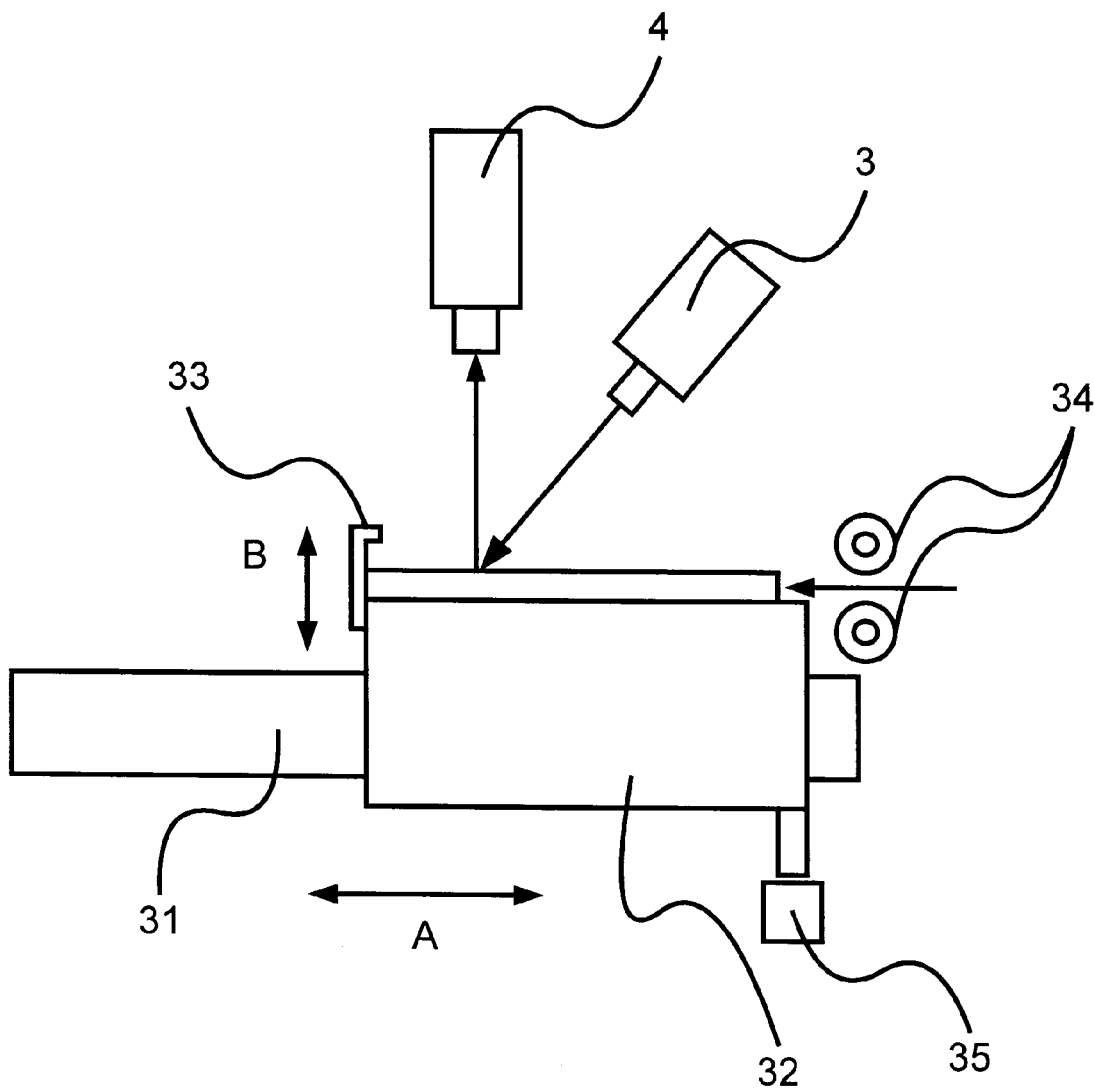
FIG. 9: This figure is a schematic diagram that shows a blow-up of the inspection apparatus section of a card manufacturing device that includes the transparent protective overlay inspection apparatus in one working embodiment of this invention in overview.

FIG. 9 is a schematic diagram that shows a blow-up of the transparent protective overlay inspection apparatus section shown in FIG. 8 in overview.

The conveyor rail 31 and the stage 32 that moves on it are the main components of the direct drive mechanism. Direct drive mechanisms are well known and often employ feed screws, air cylinders or the like in designs. A home sensor 35 is also provided to detect when the stage 32 is in the home position. The device works more or less as follows. A card which has been recorded with images and text and had a transparent protective overlay placed on it which needs inspection is brought in from the right hand side of the figure on conveyor rollers 34 placed on stage 32. Next, a clamp mechanism 33 that had previously been raised descends in the direction of arrow B and clamps onto the card. Stage 32 is then moved toward the left in the figure by the aforementioned direct drive mechanism and the light projected by the projector unit irradiates the areas to be inspected in sequence and the reflected light is fetched by the image pick-up camera and processed. After the entire inspection area has been irradiated, stage 32 moves at least to the position where reception of reflected light ends. Incidentally, the positions irradiated and the distance the stage is moved can be determined by calculating the distance the stage is moved from the home position by the direct drive mechanism. There are many techniques well known for determining the location where the inspection ends such as installing a detection sensor to find the position of stage 32 that corresponds to the end position for the inspection area.

Next, the card is freed by raising clamp mechanism 33 (not shown in figure) and removed from the stage 32 by the card conveyor mechanism.

The intensity distribution data for reflected light received by the image pick-up camera is transmitted to the data processing unit as digital data and processed according to a predetermined algorithm to determine if the quality of the transparent protective overlay passes or fails. The algorithm may for example, be a simple process, such as, whether the intensity is higher than the decided slice level or lower than that level, or whether the intensity is in the decided range or out of that range in other cases. Other cases, may include, for example, inspection of a transparent protective overlay having a bubble defect. The process by which the data is fetched, transmitted to the data processing unit, and processed to determine whether the transparent protective overlay quality passes or fails can be performed in parallel to the aforementioned moving of the card, irradiation with light, and fetching of the reflected light. Alternatively, it can be performed afterwards. To produce and inspect the greatest number of cards in the shortest period of time, the parallel method is more advantageous.

Products which pass the inspection are conveyed to a stacker that holds only passed items while failing products are conveyed to a stacker that holds only defective products. A separating mechanism must be added to the conveyor device to perform this task (not shown).

It can therefore be appreciated that a new and novel method and apparatus for inspecting the quality of protective overlays has been described. It will be appreciated by those skilled in the art that, given the teaching herein, numerous alternatives and equivalents will be seen to exist which incorporate the invention disclosed hereby. For instance, the device is not limited to inspection of transparent protective overlays, but may be used to inspect the quality of a variety of different types of surfaces. As a result, the invention is not to be limited by the foregoing exemplary embodiments, but only by the following claims.

We claim:

1. A method of inspecting transparent protective overlays comprising the steps of:
   irradiating a substrate surface onto which a transparent protective overlay that has characteristics of responding to a specific wavelength band with a light that has a peak in the specific wavelength band;
   detecting the intensity distribution of the light on the substrate surface which varies according to whether the formation of the transparent protective overlay is good or defective because of characteristics of the irradiated light and the transparent protective overlay, and
   determining the quality of the transparent protective overlay formed on the substrate surface based on the step of detecting a distribution of the light intensity.

2. The method of inspecting transparent protective overlays as recited in claim 1, wherein the transparent protective overlay includes an absorbent material that absorbs light of a specific wavelength band.

3. The method of inspecting transparent protective overlays as recited in claim 2, wherein the light of the specific wavelength band is either ultraviolet or infrared light and the light intensity distribution is obtained from light reflected from said transparent protective overlay composed of either the ultraviolet or infrared light.

4. The method of inspecting transparent protective overlays as recited in claim 1, wherein the transparent protective overlay contains a marker material that emits light in response to light of a specific wavelength band, and wherein the light intensity distribution is obtained from the light emitted by the marker material.

5. The method of inspecting transparent protective overlays as recited in claim 4, wherein the light of the specific wavelength band is ultraviolet light, and wherein the marker material emits light in response to the ultraviolet light wavelength area.

6. The method of inspecting transparent protective overlays as recited in claim 1, wherein the step of inspecting the transparent protective overlay inspects the transparent overlay formed on a card.

7. The method of inspecting transparent protective overlays as recited in claim 6, wherein information protected by the transparent protective overlay being recorded using sublimation dyes as coloring material, and wherein the ultraviolet absorbing material being diffused in at least one of the layers of said transparent protective overlays.

8. A method of inspecting transparent protective overlays formed on card substrates comprising the steps of:
   printing information on a card substrate;
   placing over the card a transparent protective overlay that has characteristics of responding to a specific wavelength band;
   irradiating the card substrate surface onto which is formed the transparent protective overlay with a light that has a peak in the specific wavelength band;
   detecting the intensity distribution of the light on the card substrate surface which varies according to whether the formation of said transparent protective overlay is good or defective because of the irradiated light and the characteristics of said transparent protective overlay; and
   inspecting the quality of the transparent protective overlay formed on the substrate surface based on the step of detecting the distribution of the light intensity.

9. The method as recited in claim 8, wherein the transparent protective overlays formed on card substrates with the information using sublimation dyes as coloring materials where an ultraviolet-absorbing material is diffused in at least one layer of each transparent protective overlay.

10. A transparent protective overlay inspection apparatus comprising:
    a means for irradiating a substrate surface onto which is formed a transparent protective overlay having the characteristics of responding to a specific wavelength band with light that peaks in the specific wavelength band;
    a means for receiving light that detects the intensity distribution of light in the transparent protective overlay created by a variation between good and defective areas of the transparent protective overlay detected by light irradiated from the irradiation means and the characteristics of the transparent protective overlay; and
    a means for determining whether the quality of the transparent protective overlay formed on the substrate surface is good or defective based on the light intensity distribution detected by the light-receiving means.

11. The transparent protective overlay inspection apparatus as recited in claim 10,
    wherein the transparent protective overlay includes an absorbing material that absorbs light in a specific wavelength band;
    wherein the light-receiving means receives a reflection from the surface of the substrate of the light irradiated by the irradiation means, and wherein the determination means determines whether the quality of the transparent protective layer is good or defective by converting the intensity of the reflected light received by the receiving light means to electrical signals and comparing those signals to reference signals.

12. The transparent protective overlay inspection apparatus as recited in claim 11, wherein the transparent protective overlay includes a marker material that emits light in response to light in a specific wavelength band, the light-receiving means receives light emitted from the marker material in response to light shone onto it by the irradiation means; and wherein the determination means determines whether the quality of the transparent protective overlay is good or defective by converting the intensity of the light received by the light-receiving means and comparing those electrical signals to reference signals.

13. The transparent protective overlay inspection apparatus as recited in claim 9, wherein the transparent protective layer is characterized by light that has its peak in the specific wavelength band of either ultraviolet or infrared light.

14. The transparent protective overlay inspection apparatus as recited in claim 9, wherein the information protected by the transparent protective overlay being recorded using sublimation dyes as coloring materials where an ultraviolet-absorbing material is diffused in at least one layer of said transparent protective overlay and the light having its peak in the specific wavelength band of ultraviolet light.

15. The transparent protective overlay inspection apparatus as recited in claim 9, wherein the transparent protective overlay is formed on a card substrate and said transparent protective overlay is inspected.

16. The transparent protective overlay inspection apparatus as recited in claim 15 comprising:

a printing unit that converts information such as images, text, symbols, and the like separately or together into electronic data and prints information such as images, text, symbols, and the like onto a card substrate based on the electronic data;

an overlay transfer unit that places the transparent protective overlay on the printed surface;

a card substrate supply unit that successively feeds card substrate into the printing unit;

a printed card conveyor unit that successively conveys printed card substrate from the printing unit to the overlay transfer unit;

a post-overlay-transfer card conveyor unit that successively conveys cards with transparent protective overlays placed on them by overlay transfer to the overlay transfer unit; and an inspected card conveyor separator unit that removes inspected cards that have undergone inspection from the transparent protective overlay inspection apparatus and conveys them to a stacker for passed products and a stacker for defective products.

17. A transparent protective overlay inspection apparatus comprising:

a means for irradiating a substrate surface onto which is formed a transparent protective overlay having the characteristic of responding to a specific wavelength band with light that peaks in said specific wavelength band;

a means for receiving light that detects the intensity distribution of light in the transparent protective overlay created by the variation in good and defective areas of the transparent protective overlay identified by the light irradiated from said irradiation means and said characteristics of said transparent protective overlay;

a means for determining whether the quality of the transparent protective overlay formed on the substrate surface is good or defective based on the light intensity distribution detected by the light-receiving means, where the means for irradiating has a light source that has a peak in a wavelength band different from the specific wavelength band, and the light-receiving means includes an optical system and image pick-up element of light in the wavelength band of said light source and a filter that passes light in said wavelength band; and a means for detecting images on the substrate that can distinguish images in the specific wavelength band from images such as text and images printed on the substrate surface using said filter to detect said printed text and images.

18. The transparent protective overlay inspection apparatus as recited in claim 17, wherein the information protected by the transparent protective overlay being recorded using sublimation dyes as coloring materials where an ultraviolet-absorbing material is diffused in at least one layer of said transparent protective overlay and the light having its peak in the specific wavelength band being ultraviolet light.

19. The transparent protective overlay inspection apparatus as recited in claim 17, wherein the transparent protective overlays are inspected where the transparent protective overlays are formed on card substrates.

20. The transparent protective overlay inspection apparatus as recited in claim 18, wherein the transparent protective overlays are inspected where the transparent protective overlays are formed on card substrates.

21. A transparent protective overlay inspection apparatus comprising:

a light projection unit disposed to irradiate the surface of an object to be inspected on which is formed a protective overlay;

a light receiver unit disposed to receive light originating from the light projection unit and reflected from the protective overlay, wherein the light receiver unit detects the intensity distribution of light reflected from the protective overlay created by a variation between acceptable and defective areas of the protective overlay; and a data processing device coupled to the light receiver unit and adapted to determine, based upon the intensity of the received light, if the protective overlay is acceptable or defective based on the measured comparison of the intensity distribution of the light to a predetermined light intensity level.

* * * * *